United States Patent [19]
Fischell et al.

[11] Patent Number: 5,389,090
[45] Date of Patent: Feb. 14, 1995

[54] GUIDING CATHETER WITH STRAIGHTENING DILATOR

[75] Inventors: Robert E. Fischell, Dayton, Md.; David R. Fischell, Fair Haven, N.J.; Tim A. Fischell, Nashville, Tenn.

[73] Assignee: Cathco, Inc., Dayton, Md.

[21] Appl. No.: 192,347

[22] Filed: Feb. 7, 1994

[51] Int. Cl.⁶ .............................................. A61M 25/00
[52] U.S. Cl. ................................... 604/280; 604/283
[58] Field of Search .................. 604/95, 165, 167, 280, 604/283, 241, 243; 606/194, 191, 192

[56] References Cited

U.S. PATENT DOCUMENTS

| | | | |
|---|---|---|---|
| 5,053,007 | 10/1991 | Euteneuer | 606/194 |
| 5,129,887 | 7/1992 | Euteneuer et al. | 604/283 X |
| 5,224,939 | 7/1993 | Holman et al. | 604/283 |
| 5,267,982 | 12/1993 | Sylvanowicz | 604/281 |
| 5,324,271 | 6/1994 | Abiuso et al. | 604/283 X |

*Primary Examiner*—John D. Yasko

[57] ABSTRACT

A guiding catheter system (10) is provided that includes a Tuohy-Borst fitting (20) attached as a one-piece construction to a guiding catheter tube (11). The guiding catheter system (10) can also include a dilator (16) and a guide wire 15. The Tuohy-Borst fitting (20) can have a side arm (14) onto which a stop cock (30) can be attached. With the stop cock (30) in its closed position, fluid flow through the side arm (14) is prevented. When the nut (22) on the Tuohy-Borst fitting (20) is tightened down so that the gland (24) in the Tuohy-Borst fitting (20) seals against the guide wire (15) and the stop cock (30) is closed, blood loss through the proximal end of the guiding catheter system (10) can be essentially eliminated. Since the Tuohy-Borst fitting (20) is integrally joined to the proximal end of the guiding catheter tube (11), the need for a separately packaged and sterilized Tuohy-Borst fitting to be screwed onto the guiding catheter's proximal end is eliminated. The dilator (16) with the guide wire (15) can be used to allow percutaneous insertion of the guiding catheter system (10) into a patient's artery without requiring an introducer sheath, thus reducing the size of the hole that is made in the wall of the artery. A smaller hole in the artery's wall reduces the possibility of post-procedure bleeding at that point where the guiding catheter system (10) is inserted.

20 Claims, 2 Drawing Sheets

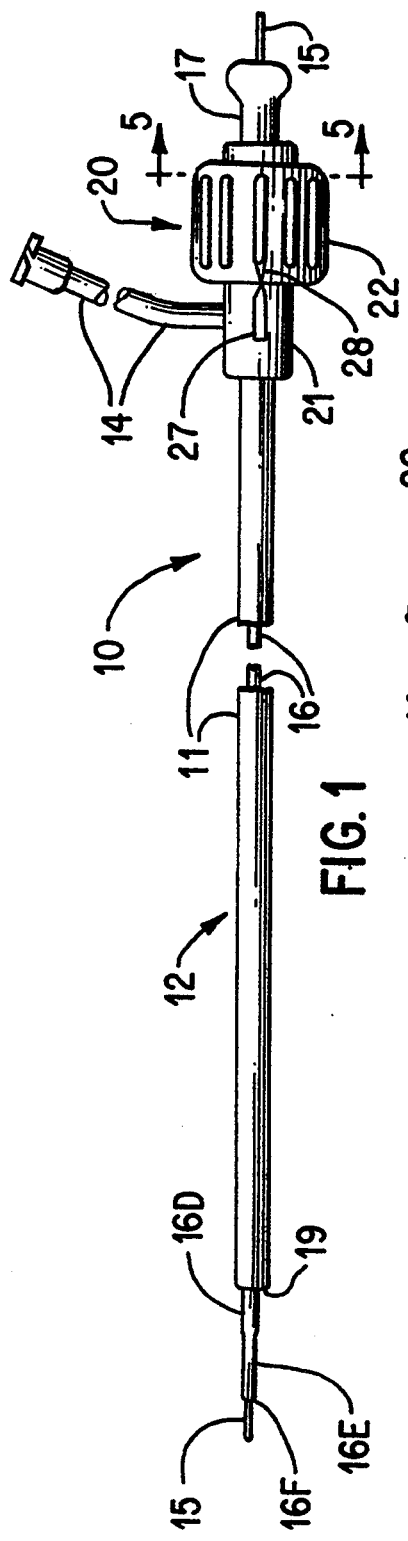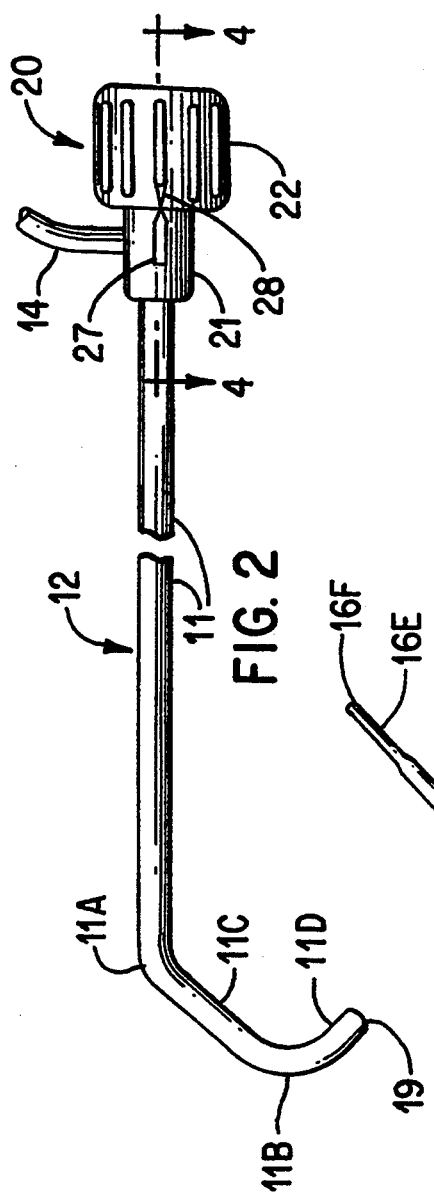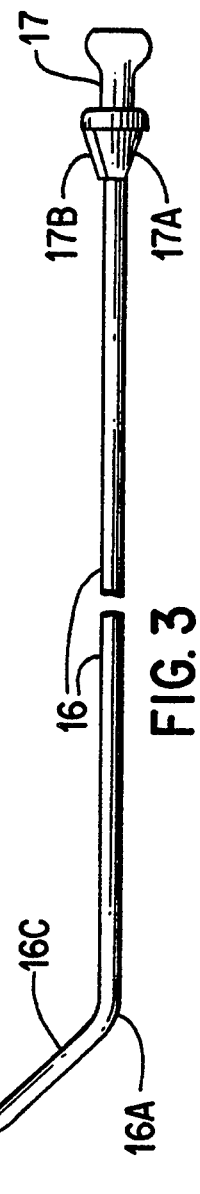

GUIDING CATHETER WITH STRAIGHTENING DILATOR

FIELD OF USE

This invention is in the field of guiding catheters for introducing guide wires and artery opening catheters into the arterial system of human beings.

BACKGROUND OF THE INVENTION

To access the coronary (or other) arteries for a variety of purposes including dilation of stenoses, an interventional cardiologist would first introducer a guide wire through an arterial access needle puncture at the groin, and then an introducer sheath with dilator would be advanced over the guide wire and into the lumen of the femoral artery. The dilator would then be removed and a guiding catheter would be advanced through the sheath and over the guide wire until the guiding catheter's distal end would be situated in the ostium of a coronary artery. An artery opening catheter (such as a balloon angioplasty catheter or atherectomy catheter) would then be advanced through the guiding catheter, and an angioplasty or atherectomy procedure would be performed to open an arterial stenosis. In recent practice, intra-arterial stents are placed at the site of the opened stenosis by means of a stent delivery catheter. These stent delivery catheters require a fairly large diameter guiding catheter; typically 9 or 10 French size. Since the outer diameter of the sheath through which the guiding catheter is inserted is typically 2 French sizes larger then the size of the guiding catheter, a fairly large diameter hole must be made through the wall of the femoral artery. These larger size holes often lead to excessive bleeding at the groin after the sheath is removed.

To perform an artery opening procedure with a guiding catheter, it is also necessary to attach a Tuohy-Borst "Y" adaptor onto the guiding catheter's proximal end. The introducer sheath and Tuohy-Borst "Y" adaptor are each components that require additional time for the interventional cardiologist to properly place, and they add to the cost of performing artery opening procedures.

SUMMARY OF THE PRESENT INVENTION

The present invention is an improved guiding catheter that eliminates the need for an introducer sheath or a Tuohy-Borst "Y" adaptor, thus reducing the time and expense for performing artery opening procedures. Furthermore, the guiding catheter with straightening dilator as described herein allows the hole in the wall of the femoral artery to be approximately 2 French sizes smaller in diameter as compared to the hole that would be created if an introducer sheath is also used.

The advantages of the present invention are accomplished by utilizing a guiding catheter with a dilator that has a curved distal section that can be used to straighten the distal section of the guiding catheter as it is advanced through the arterial system. The guiding catheter plus dilator can then be used as an introducer sheath to enter the femoral artery by being advanced over a previously placed guide wire. Once the distal ends of the dilator and guiding catheter are placed near the ostium of the coronary artery, the dilator and guide wire are withdrawn which allows the guiding catheter to assume its normally bent shape (e.g., a Judkin's bend) near its distal end. The cardiologist can then, by well known techniques, place the guiding catheter's distal end in the ostium of a coronary artery. Any of several well known procedures can then be performed including angiography, balloon angioplasty, atherectomy or stent placement.

The guiding catheter of the present invention also utilizes the unique feature of a Tuohy-Borst fitting with a side arm at the guiding catheter's proximal end. This capability obviates the need for attaching a separate Tuohy-Borst fitting at the guiding catheter's proximal end to accomplish the same functions of arterial access with minimum bleeding. The guiding catheter's Tuohy-Borst fitting could be tightened around guide wires or the shaft of catheters that are advanced through the guiding catheter. The side arm would typically terminate in a female Luer fitting that can be attached to a manifold for the introduction of saline solution, contrast medium or medications. Thus, the Tuohy-Borst fitting with side arm at the guiding catheter's proximal end eliminates the need for a separate Tuohy-Borst fitting.

Thus, it is an objective of the present invention to allow placement of a guiding catheter without requiring insertion of the guiding catheter through an introducer sheath thus allowing a smaller hole to be made in the wall of the femoral artery.

Another objective of this invention is to eliminate the need for a separate Tuohy-Borst fitting by placing a Tuohy-Borst fitting and side arm at the guiding catheter's proximal end.

Still another objective of the invention is to use a dilator with a guiding catheter for placement of the guiding catheter without requiting an introducer sheath.

Still another objective of the invention is to utilize a dilator having a curved distal section that when placed inside a guiding catheter causes the dilator-guiding catheter assembly to be essentially straight for easy insertion through the arterial system.

Still another objective of the invention is to use a straightening dilator of increased stiffness so that it straightens the distal section of a guiding catheter which also has increased stiffness at its distal section so that when the dilator is withdrawn, the distal section of the guiding catheter will more strongly maintain its placement in the ostium of a coronary artery.

Still another objective of the invention is to reduce the cost and time required for performing arterial interventional procedures.

Still another objective of the invention is to eliminate excessive bleeding through the guiding catheter when it is being inserted.

These and other objects and advantages of this invention will become obvious to a person of ordinary skill in this art upon reading of the detailed description of this invention including the associated drawings.

BRIEF DESCRIPTION OF THE DRAWINGS

FIG. 1 is a side view of a guiding catheter system including a guide wire, straightening dilator and a guiding catheter with Tuohy-Borst fitting.

FIG. 2 is a side view of a guiding catheter with Tuohy-Borst fitting at its proximal end.

FIG. 3 is a side view of a straightening dilator.

DETAILED DESCRIPTION OF THE INVENTION

Figure 4:
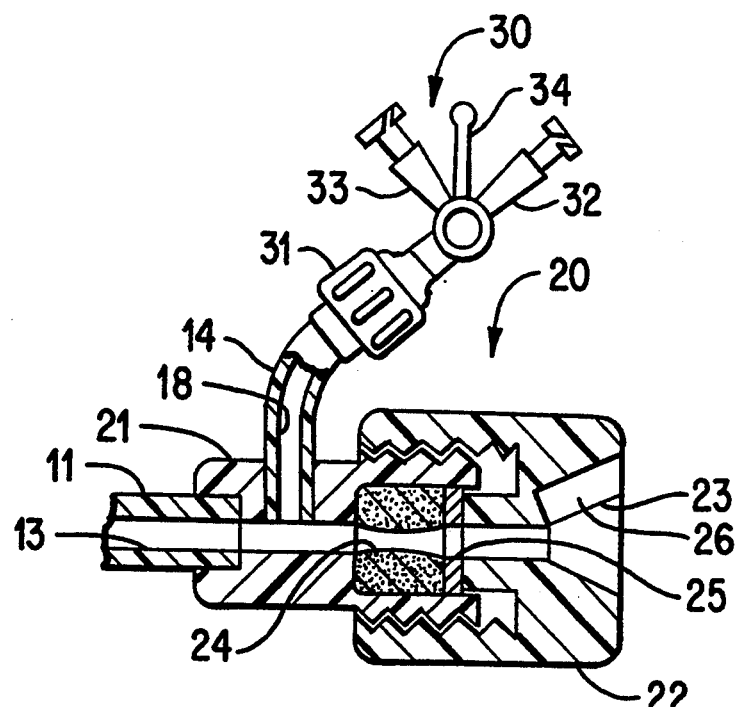
FIG. 4 is an enlarged partial longitudinal cross section of the proximal end of the guiding catheter at section 4—4 of FIG. 2.

FIGS. 1, 2 and 3 illustrate the guiding catheter system 10 having a guiding catheter 12 with an elongated tube 11 with a tapered distal end 19, and a Tuohy-Borst fitting 20, a guide wire 15 and a straightening dilator 16. The dilator 16 (particularly as shown in FIG. 3) has a distal section with a first bend 16A and a second bend 16B, and a first distal section 16C, a second section 16D, and a third section 16E that is aligned with section 16D but of smaller diameter. The section 16E has a tapered distal end 16F designed to fit snugly around a guide wire as that distal end 16F is advanced through the arterial system. It should be understood that there could be only one bend, or more than two bends at this distal section of the dilator. All the sections 16 of the dilator are designed to fit slideably within the interior lumen of the guiding catheter tube 11. The dilator also has at its proximal end a handle 17 with a cone 17A having a key 17B for mating with the threaded nut 22 of the Tuohy-Borst fitting 20 as seen in FIG. 5.

As seen in FIG. 2, the guiding catheter tube 11 has bends 11A and 11B along a distal section, and furthermore has distal sections 11C and 11D. The guiding catheter 12 also has a Tuohy-Borst fitting 20 is integrally attached as a one-piece construction with the tube 12 and at its proximal end. As seen in FIGS. 1, 2 and 4, the Tuohy-Borst fitting 20 has a threaded base 21, a side arm 14 having a female Luer lock fitting, a threaded nut 22 with conical entry lumen 23, a soft elastomer gland 24 and a comparatively hard washer 25. When the nut 22 is not tightened down, the gland 24 is not compressed and the lumen 23 is in fluid communication with the lumen 13 of the elongated tube 11 and the lumen 18 of the side arm 14. When the nut 22 is screwed into the threaded base 21, the washer 25 compresses the soft elastomer gland 24 which can then fit snugly around a guide wire or a dilator or the shaft of an artery opening catheter or stent delivery catheter. Furthermore, when the nut 22 is fully screwed onto the threaded base 21, the central lumen of the gland 24 can be totally closed so that no blood will leak out of the guiding catheter's proximal end with no guide wire or catheter placed through that gland 24.

Figure 5:
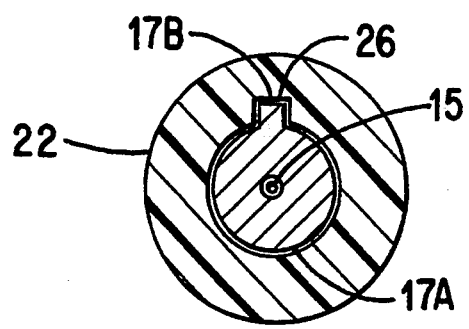
FIG. 5 is an enlarged transverse cross section of the Tuohy-Borst fitting at section 5—5 of FIG. 1.

FIGS. 4 and 5 also show a keyway 26 in the nut 22 which is adapted to mate with the key 17B of the dilator handle 17. This alignment guarantees that the bends in the distal sections of the guiding catheter tube 11 and the dilator 16 oppose each other so as to straighten the guiding catheter system 10 as shown in FIG. 1. In this position, the guiding catheter with dilator 16 in place can be readily advanced over the guide wire 15 until the distal end of the guiding catheter 12 is located near the ostium of the artery (e.g., a coronary artery) to which access is desired. The dilator 16 can then be withdrawn and the guiding catheter 12 will assume its desired distal section shape as shown in FIG. 2. The interventionalist can then place the guiding catheter's distal end 19 into the ostium of that artery.

As shown in FIGS. 1 and 2, the threaded base 21 can include an indicator mark 27 which, when aligned with an indicator mark 28 on the nut 22, informs the operator that the tube 11 and dilator 16 are positioned so that together they form a straight distal end section as shown in FIG. 1. When the nut is rotated 180° away from the position shown in FIGS. 1 and 2, the distal end section of the tube 11 will be as shown in FIG. 2 even when the dilator 16 is placed therein. Between the positions when the indicator marks 27 and 28 are aligned or at 180° from each other, the distal end section of the guiding catheter system 10 will be formed into some intermediate curved shape. Such intermediate shapes may be of value in advancing the distal end of the guiding catheter system 10 through the arterial vasculature.

It is also conceived that a straight dilator without a key could be used with the guiding catheter 12 that is shown in FIG. 2. Such a dilator would tend to straighten the guiding catheter 12. The stiffer the distal section of such a dilator, the straighter would be the distal section of the assembly of the dilator with the guiding catheter 12. Of course, when such a straight (or curved) dilator would be pulled out, the distal section of the guiding catheter 12 would assume its proper shape as generally illustrated in FIG. 2.

After the dilator is fully withdrawn and the guiding catheter's distal end is placed into the ostium of an artery, a balloon angioplasty catheter or an atherectomy catheter (i.e., an artery opening catheter) could be placed through the guiding catheter 12 and a selected stenosis in that artery could be opened to improve blood flow. The artery opening catheter could then be withdrawn, and a stent delivery catheter could be used to place a stent at the site of the opened stenosis. The stent delivery catheter would then be removed and the guiding catheter system 10 could be removed.

If continued access to the artery is desired, the guide wire 15 could remain in place after the guiding catheter system 10 is removed, and an introducer sheath having the same outside diameter as the guiding catheter tube 11 could be inserted through the skin at the groin and into the femoral artery. Although this would then require the additional component of an introducer sheath, the procedure would be improved because the hole required to be made through the wall of the femoral artery would be two French sizes smaller. For example, if a 10 French guiding catheter were used, only an 8 French introducer sheath would be required after the guiding catheter is removed since they both have approximately the same outside diameter. If it were initially required to place the guiding catheter 12 through an introducer sheath, a 10 French guiding catheter would require a 10 French introducer sheath which obviously is two French sizes larger in outside diameter as compared to an 8 French sheath that could be used after the guiding catheter is fully withdrawn from the body.

It should also be pointed out that the Tuohy-Borst fitting 20 with side arm 14 precludes the need for using a Tuohy-Borst "Y" adaptor that would normally be joined to the female Luer lock fitting at the proximal end of currently used guiding catheters. The manifold for fluid delivery would be connected to the side arm 14 and the Tuohy-Borst fitting would be used in the manner previously described. A stop cock 30 having a Luer nut 31, side ports 33 and 34 and operating lever 34 (shown in FIG. 4 in its closed position to prevent the outflow of blood) could also be placed at the proximal end of side arm 14. Even without the use of a dilator, (i.e., the guiding catheter 12 would be inserted through an introducer sheath) a guiding catheter 12 as shown in FIG. 2 without a dilator would offer an advantage over existing guiding catheters in that a Tuohy-Borst "Y" adaptor would not be required.

Thus the objectives of using a guiding catheter without passing it through an intoducer sheath and the elimination of the need for a separate Tuohy-Borst "Y" adaptor have been shown. Furthermore, the objective of inserting a guiding catheter over a guide wire without the free release of blood through the guiding catheter's proximal end can be accomplished by compressing the gland 24 around the guide wire as the guiding catheter is advanced through the arterial system.

Although the discussion herein has been principally concerned with coronary guiding catheter systems, the present invention is well suited for the placement of guiding catheters into the ostia of other arteries such as the carotid and renal arteries as well as coronary artery bypass grafts.

Figure 6A:
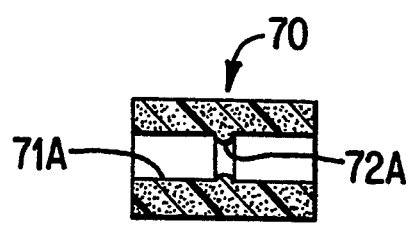
FIG. 6A is a cross section of a Tuohy-Borst gland with a half "O" ring, with the gland shown in a fully open position.
Figure 6B:
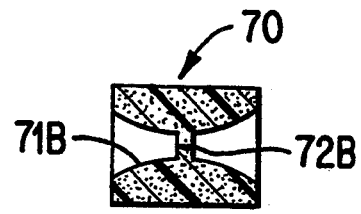
FIG. 6B is a cross section of a Tuohy-Borst gland with a half "O" ring with the gland in a fully closed position.

FIGS. 6A and 6B illustrate an alterative design for the soft elastomer gland of a Tuohy-Borst fitting. Specifically, FIG. 6A shows a gland 70 in its open (not compressed) state. The gland 70 has a generally cylindrical interior surface 71A on which is placed a half "O" ring 72A. When a nut 22 of FIG. 1 is tightened, the gland 70 can be deformed to the shape shown in FIG. 6B wherein a highly curved interior surface 71B is formed with the half "O" ring 72B being distorted to a closed or nearly dosed position as shown in FIG. 6B.

This invention envisions that the Tuohy-Borst gland (such as glands 24 or 70) could be fabricated from a soft elastomer such as a low durometer silicone rubber. Furthermore, powdered Teflon or powdered graphite could be incorporated into the soft elastomer to improve its lubricity.

Various other modifications, adaptations, and alternative designs are of course possible in light of the above teachings. Therefore, it should be understood at this time that within the scope of the appended claims, the invention may be practiced otherwise than as specifically described herein.

What is claimed is:

1. A guiding catheter system for the insertion of guide wires and catheters into a vessel of a human body comprising;
   an elongated hollow tube having proximal and distal ends and a distal section, the hollow tube's distal end being tapered for easy introduction into a blood vessel and the distal section having a bend adapted to facilitate introduction into and retention into the ostium of an artery;
   a dilator having an elongated body and proximal and distal ends and a distal section and having a handle located at the dilator's proximal end, the dilator being tapered at its distal end; and,
   a Tuohy-Borst fitting integrally attached as a one-piece construction at the hollow tube's proximal end, the Tuohy-Borst fitting including a threaded base, a threaded nut and an elastomer gland that can be tightened around the dilator by screwing the threaded nut onto the threaded base.

2. The guiding catheter system of claim 1 wherein the dilator has a central lumen for the placement therethrough of a guide wire.

3. The guiding catheter system of claim 1 including a flexible guide wire for insertion through the dilator's central lumen.

4. The guiding catheter system of claim 1 wherein the distal sections of the elongated hollow tube and the dilator are each curved.

5. The guiding catheter system of claim 4 wherein the dilator is placed within the elongated tube to form an essentially straight, tube-dilator assembly when an indicator mark on the threaded base is aligned with an indicator mark on the threaded nut.

6. The guiding catheter system of claim 1, wherein the distal sections of the elongated hollow tube and the dilator are each curved and further, the dilator includes a key at its proximal end that fits into a keyway in the threaded nut of the Tuohy-Borst fitting.

7. The guiding catheter system of claim 1 wherein the entire length of the dilator is straight.

8. The guiding catheter system of claim 1 wherein the Tuohy-Borst fitting has a side arm tube joined to the Tuohy-Borst fitting's threaded base, the side arm tube having distal and proximal ends.

9. The guiding catheter system of claim 7 wherein the side arm tube has a female Luer fitting at its proximal end.

10. The guiding catheter system of claim 7 wherein the side arm tube has a stop cock at its proximal end.

11. The guiding catheter system of claim 1 wherein the gland of the Tuohy-Borst fitting includes a half "O" ring on its interior surface.

12. The guiding catheter system of claim 1 wherein the gland of the Tuohy-Borst fitting is fabricated from a soft elastomer which elastomer includes a powdered Teflon.

13. The guiding catheter system of claim 1 Wherein the gland of the Tuohy-Borst fitting is fabricated from a soft elastomer which elastomer includes a powdered graphite.

14. A guiding catheter system for the insertion of guide wires and catheters into a vessel of a human body comprising;
   an elongated hollow tube having proximal and distal ends and a distal section, the hollow tube's distal end being tapered for easy introduction into a blood vessel and the distal section having a bend adapted to facilitate introduction into and retention in the ostium of an artery; and
   a Tuohy-Borst fitting integrally attached as a one-piece construction at the hollow tube's proximal end, the Tuohy-Borst fitting including a threaded base, a threaded nut and an elastomer gland having an interior lumen, the Tuohy-Borst fitting being capable of reducing the area of the lumen of the elastomer gland by screwing the threaded nut further onto the threaded base.

15. The guiding catheter system of claim 14 wherein the Tuohy-Borst fitting has a side arm tube joined to the Tuohy-Borst fitting's threaded base, the side and tube having distal and proximal ends.

16. The guiding catheter system of claim 15 wherein the side arm tube has a female Luer fitting at its proximal end.

17. The guiding catheter system of claim 15 wherein the side arm tube has a stop cock at its proximal end.

18. The guiding catheter system of claim 14 wherein the gland of the Tuohy-Borst fitting includes a half "O" ring on its interior surface.

19. The guiding catheter system of claim 14 wherein the gland of the Tuohy-Borst fitting is fabricated from a soft elastomer which elastomer includes a powdered Teflon.

20. The guiding catheter system of claim 14 Wherein the gland of the Tuohy-Borst fitting is fabricated from a soft elastomer which elastomer includes a powdered graphite.

* * * * *